United States Patent [19]

Yagi et al.

[11] Patent Number: 5,262,101
[45] Date of Patent: * Nov. 16, 1993

[54] BANK QUANTITY MONITORING METHOD AND APPARATUS, SHEET FORMING METHOD AND APPARATUS, AND SHEET TEMPERATURE MEASURING METHOD AND APPARATUS

[75] Inventors: Masayuki Yagi; Toshihiko Kusago, both of Numazu, Japan

[73] Assignee: Toshiba Kikai Kabushiki Kaisha, Tokyo, Japan

[*] Notice: The portion of the term of this patent subsequent to Oct. 27, 2009 has been disclaimed.

[21] Appl. No.: 890,085

[22] Filed: May 29, 1992

Related U.S. Application Data

[62] Division of Ser. No. 521,360, May 10, 1990, Pat. No. 5,158,724.

[30] Foreign Application Priority Data

Nov. 21, 1989 [JP] Japan .................. 1-302779

[51] Int. Cl.⁵ .............................. B29C 47/92
[52] U.S. Cl. ..................... 264/40.1; 100/168; 100/176; 264/40.2; 264/40.5; 264/40.6; 264/40.7; 264/211.12; 374/124; 374/137; 374/153; 374/154; 425/141; 425/143; 425/145; 425/327; 425/367; 425/382.3
[58] Field of Search ............... 264/40.1, 40.2, 40.5, 264/40.6, 40.7, 175, 210.2, 211.12; 425/135, 141, 143, 144, 145, 194, 200, 327, 366, 367, 377, 382.3; 100/168, 176; 374/124, 137, 153, 154

[56] References Cited

U.S. PATENT DOCUMENTS 3,274,308 9/1966 Freeman et al. .................. 264/40.5
4,871,493 10/1989 Goto ................................ 264/40.6

FOREIGN PATENT DOCUMENTS

| 48-47955 | 7/1973 | Japan . | |
| 53-28657 | 3/1978 | Japan . | |
| 61-76337 | 4/1986 | Japan | 425/143 |
| 62-28216 | 2/1987 | Japan | 264/40.5 |

Primary Examiner—Leo B. Tentoni
Attorney, Agent, or Firm—Stevens, Davis, Miller & Mosher

[57] ABSTRACT

A plastic material, controlled at a desired temperature, is fed on an upstream side of a gap between a pair of rotating forming rolls arrayed almost in parallel and controlled at a desired temperature from a device for feeding the plastic material. The plastic material is pressed and formed into a sheet by the forming rolls therebetween while forming a bank or an accumulation of the plastic material on an upstream side of the gap of the forming rolls and is carried out on a downstream side of the gap. The bank quantity monitoring is performed by measuring a temperature of the sheet carried out through the gap of the forming rolls and estimating the quantity of the bank in accordance with measured temperature information. The sheet formation is performed by measuring a temperature of the sheet carried out through the gap of the forming rolls and controlling various forming conditions according to a measured temperature information. The sheet temperature measurement is performed by measuring a temperature of the sheet by directing said non-contacted temperature measuring means against an inner part of a wedge-shaped space formed by a surface of the sheet carried out of the gap and a surface of the forming roll facing on the surface of the sheet at a slight gap therebetween.

38 Claims, 7 Drawing Sheets

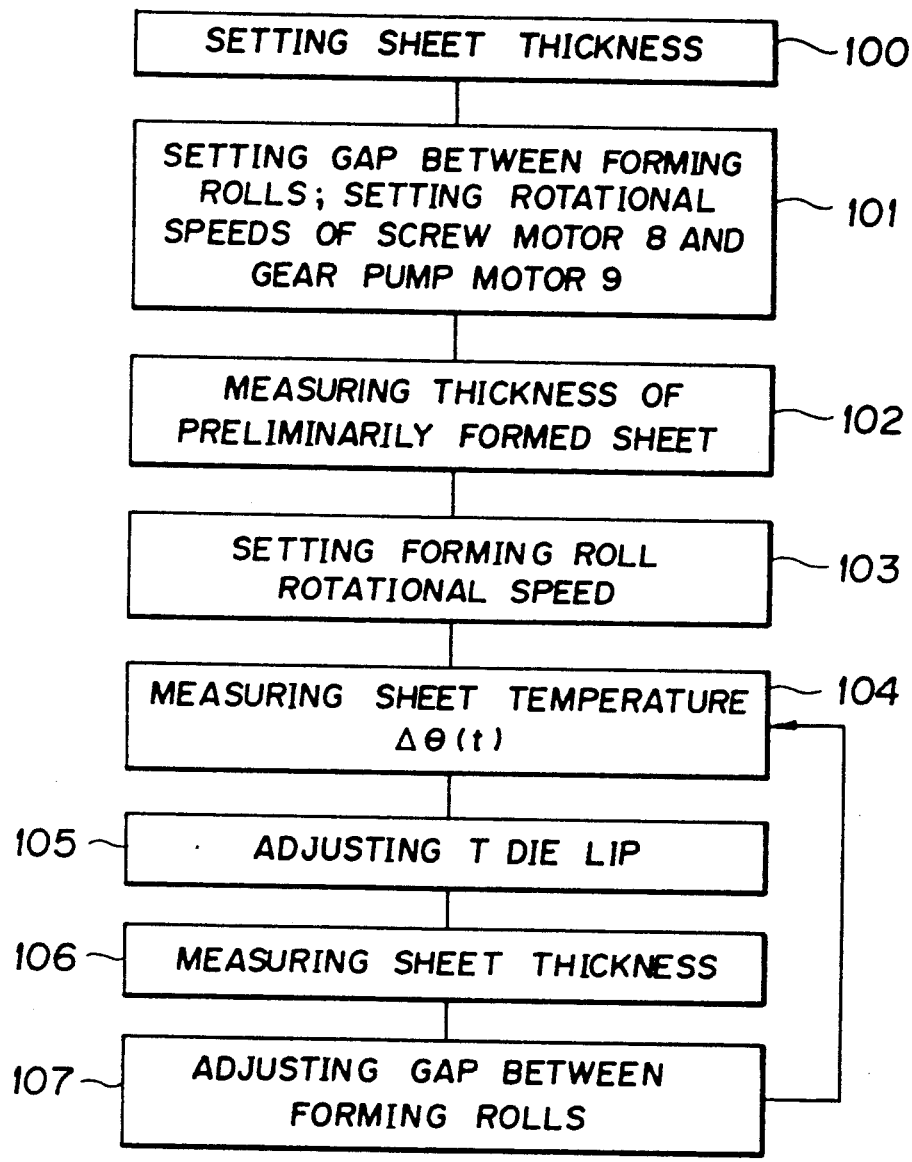

BANK QUANTITY MONITORING METHOD AND APPARATUS, SHEET FORMING METHOD AND APPARATUS, AND SHEET TEMPERATURE MEASURING METHOD AND APPARATUS

This is a division of application Ser. No. 07/521,360, filed May 10, 1990, now U.S. Pat. No. 5,158,724.

BACKGROUND OF THE INVENTION

The present invention relates to a monitoring method for quantity of bank, a forming method for a sheet and measuring method for sheet temperature thereof and apparatus therefor and, more particularly, to a monitoring method for quantity of bank and an apparatus therefor, a forming method for a sheet and an apparatus therefor, and further a measuring method and apparatus for sheet temperature preferable for putting the aforementioned monitoring method and sheet forming method into practice in a sheet forming wherein a plastic material such as plastics, rubber or the like; controlled at a desired temperature; is fed on an upstream side of a gap between a pair of forming rolls arrayed almost in parallel and controlled at a desired temperature each relative to a flat die; connected to an extruding machine and having a slit outflow portion, the plastic material being pressed and formed into a sheet on the forming rolls in the gap therebetween, while forming a bank or an accumulation of the plastic material on an upstream side of the gap of the forming rolls, and is carried out on a downstream side of the gap.

In the aforementioned sheet forming method, a plastic material at a desired temperature is fed on an upstream side of a gap between a pair of two forming roll which rotate in reverse directions and controlled at a desired temperature; from a flat die connected to an extruding machine, an accumulation of the plastic material, namely a bank, being formed on the upstream side of the gap, the plastic material forming the bank being drawn into the gap of the narrowest portion (hereinafter simply called "gap") during rotation of the forming rolls, thereby pressing and forming the plastic material and carrying it out on a downstream side of the gap as a sheet. One of essentials exerting an influence on the quality of the sheet obtained through the sheet forming method is to keep a quantity of bank or a height of the bank from the center of the gap at an appropriate value. A deficiency in the quantity of bank may invite a surface defect called "shrink mark", and on the contrary in the case where the quantity of bank is excessive, a surface defect of wavy marks, called "bank marks", which extends breadthwise of the sheet at intervals in the direction where the sheet runs; arises, and further the forming rolls are bent to deteriorate a thickness distribution in the transverse direction of the running length of the sheet. To produce the sheet having desired characteristics without causing the aforementioned surface defects and the deterioration of thickness distribution as mentioned above, it is necessary that the quantity of bank (height) be controlled more accurately.

Now, therefore, as disclosed in Japanese Patent Laid-Open No. 47955/1973 and Japanese Patent Laid-Open No. 28657/1978, there proposed is an apparatus wherein a light is applied to the bank from either the upstream side or sideways, with the quantity of bank being measured by reflection or passage of the light, and a supply of the plastic material from the flat die or a rotational speed of the forming rolls is controlled so as to adjust the quantity of bank to a desired value.

According to the aforementioned way of measuring the quantity of bank by the irradiation of a light, a maximum value of the quantity of bank only is obtainable from applying the light sideways, but a distribution in the cross transverse direction cannot be measured. Thus, when applying the light from the upstream side, the distribution in the cross direction or preferably of a whole area can be measured. However, an upstream side of the bank is narrowed like a valley by the forming rolls, the flat die being disposed as close as possible to the bank to close an upstream side of the valley-like portion for the most part, and practically, the bank is formed slightly in the inner part of the gap, therefore such measurement involves difficulty. Now, therefore, the aforementioned sheet forming technique owes much to experience of operators hitherto, and thus it is difficult to produce a quality sheet easily and accurately.

SUMMARY OF THE INVENTION

Objects of the present invention are to provide a method and apparatus for monitoring the quantity of bank and capable of quantifying the aforementioned quantity of bank accurately.

Another object of the present invention is to provide a method and apparatus for forming sheets capable of forming a quality sheet according to the quantity of bank measured accurately as above.

A further object of the present invention is to provide a method and apparatus for measuring sheet temperature for quantifying the quantity of bank more accurately.

To attain the aforementioned objects, according to the present invention, in one aspect, there is provided a monitoring method for quantity of bank in a sheet forming wherein a plastic material, controlled at a desired temperature, is fed on an upstream side of a gap between a pair of rotating forming rolls, arrayed almost in parallel and controlled at a desired temperature, from a flat die connected to an extruding machine and having a slit outflow portion, the plastic material being pressed and formed into a sheet by the forming rolls in the gap therebetween while forming a bank or an accumulation of the plastic material on an upstream side of the gap of the forming rolls and being carried out on a downstream side of the gap, wherein a temperature of the sheet carried out of the gap of the forming rolls is measured, the quantity of the bank is then estimated according to a measured temperature information.

It is desirable that the temperature information of the sheet to be measured indicates a temperature distribution at least at a plurality of portions in the cross direction of the sheet carried out of the gap.

Then, it is effective that temperature information of the measured sheet be corrected according to temperature information of the plastic material fed on an upstream side of the gap, thereby estimating the quantity of bank.

Further, it is also advisable to estimate the quantity of bank by correcting temperature information of the measured sheet according to temperature information of the forming rolls.

The sheet temperature may be measured by directing non-contacted temperature measuring means against the inner part of a wedge-shaped space formed by a surface of the sheet carried out of the gap and a surface of the forming roll opposite to the sheet surface.

A monitoring apparatus for quantity of bank in a sheet forming of the present invention wherein a plastic material, controlled at a desired temperature, is fed on an upstream side of a gap between a pair of forming rolls, arrayed almost in parallel and controlled at a desired temperature each, rotating relative to a flat die connected to an extruding machine and having a slit outflow portion, the plastic material being pressed and formed into a sheet by the forming rolls in the gap therebetween as a bank or an accumulation of the plastic material, on an upstream side of the gap of the forming rolls and is carried out on a downstream side of the gap, the apparatus comprising temperature measuring means for measuring a temperature of the sheet carried out of the gap of the forming rolls and display means for loading and displaying temperature information measured by the temperature measuring means for estimating the quantity of bank.

The aforementioned temperature measuring means comprises means for measuring temperatures of at least plural portions in the cross direction of the sheet carried out of the gap of the forming rolls.

It is preferable that an arithmetic operation means part for computing a quantity of bank from the temperature information, be connected between the aforementioned temperature measuring means and display means.

It is then advisable to provide a first temperature sensor for detecting a temperature of the plastic material fed to the gap, and also to connect a measurement processing part for correcting the aforementioned temperature information according to an output of the first temperature sensor between the aforementioned temperature measuring means and display means.

Further, it is effective to provide a second temperature sensor for detecting a temperature of the forming rolls, and also to connect a measurement processing part for correcting the temperature information according to an output of the second temperature sensor between the aforementioned temperature measuring means and display means.

The aforementioned first and second temperature sensors comprise detecting temperatures of at least plural portions in the cross direction thereof.

The aforementioned temperature measuring means is an infrared-ray radiating thermometer, which is mounted to face on the inner part of a wedge-shaped space formed by a surface of the sheet carried out of the gap and a surface of the forming roll opposite to the sheet surface.

The infrared-ray radiating thermometer may be constructed so as to measure infrared-rays of an absorbing wave band of the sheet.

In another aspect of the present invention, there is provided a sheet forming method wherein a plastic material controlled at a desired temperature is fed on an upstream side of a gap between a pair of rotating forming rolls arrayed almost in parallel and controlled at a desired temperature from a flat die connected to an extruding machine and having a slit outflow portion, the plastic material being pressed and formed into a sheet by the forming rolls in the gap therebetween while forming a bank or an accumulation of the plastic material on an upstream side of the gap of the forming rolls and is carried out on a downstream side of the gap, wherein a temperature of the sheet carried out of the gap of the forming rolls is measured and, various forming conditions are controlled according to the measured temperature information.

It is preferable that any one of a or plurality of supply of the plastic material, rotational speed of the forming rolls, and gap of the forming rolls be controlled for the forming conditions.

Then, it is preferable that temperature information of the sheet to be measured indicate a temperature distribution consisting at least of plural portions in the cross direction of the sheet carried out.

It is also preferable that a comparison of a reference set temperature information to temperature information of the measured sheet be obtained so as to determine a distribution corresponding to a temperature distribution in the cross direction of the fed plastic material.

In a further aspect of the present invention, the sheet forming method of the invention may comprise:

a process for setting a thickness to work as a forming target of a sheet to be formed;

a process for initializing a supply of the plastic material from an extruding machine, and setting a gap of a pair of forming rolls for forming sheets according to the set thickness;

an initial forming process for feeding the plastic material to the gap of the forming rolls from a flat die connected to an extruding machine and having a slit outflow portion, pressing and forming the plastic material on the aforementioned forming rolls in the gap therebetween while forming a bank or an accumulation of the plastic material on an upstream side of the gap of the forming rolls and carrying it out on a downstream side of the gap as a sheet;

a process for initializing a rotational speed of the forming rolls according to a mean thickness of the sheet subjected to an initial forming; and a process for measuring a temperature of the sheet carried out of the gap of the forming rolls, including adjusting a mechanism for adjusting a distribution of flow in the cross direction, which is provided at least near the outflow portion of the flat die, so as to adjust the measured temperature information to a predetermined value correspond to a desired quantity of bank, thereby adjusting the quantity of bank which is the height of the bank from the center of the gap of the forming rolls.

It is then advisable to provide a process for measuring a thickness of the sheet carried out of the forming rolls after adjustment of the quantity of bank, and adjusting a distribution in the cross direction of the gap of the forming rolls according to a measured value.

Meanwhile, a sheet forming apparatus according to the present invention comprises an extruding machine for feeding a plastic material controlled at a desired temperature, a flat die connected to the extruding machine and having a slit outflow portion, a pair of forming rolls arrayed almost in parallel to have a predetermined gap therebetween for pressing and forming the plastic material fed from the flat die and controlled at a predetermined temperature each relatively rotating with respect to one another, and the apparatus further comprising temperature measuring means for measuring a temperature of the sheet carried out of the gap of the forming rolls and control means for controlling various objects to control optimum forming conditions according to temperature information measured by the temperature measuring means.

It is preferable that the objects to control include any one or plurality of a plastic material feed part of the extruding machine, a rotation driving part of the forming rolls and a gap adjusting part of the forming rolls.

It is then preferable that the temperature measuring means be constructed so as to generate an output in relation at least to a plurality of measuring positions in the cross direction of the sheet.

It is further preferable that the temperature measuring means be constructed so as to scan measuring portions in the cross direction of the sheet and also to generate an output in relation to each measuring position in the cross direction thereof.

Still further, it is preferable that a comparison of a reference set temperature information to temperature information of the sheet to be measured may vary according to positions in the cross direction of the sheet.

On the other hand, the extruding machine may comprise an extruder for extruding the plastic material, a flat die having a slit outflow portion, a gear pump for discharging the plastic material toward the flat die from the extruder, and the objects to control by the control means may include a rotational speed of a screw of the extruder and the gear pump.

Then, the objects to control may include a mechanism for adjusting a distribution of flow in the cross direction of the flat die connected to the extruding machine.

Further, it is preferable that the temperature measuring means be non-contact measuring means, or, particularly an infrared-ray radiating thermometer.

In a still further aspect of the present invention, there is provided a measuring method for measuring the temperature of a sheet carried out of a sheet forming apparatus wherein a plastic material, controlled at a desired temperature, is fed on an upstream side of a gap between a pair of rotating forming rolls arrayed almost in parallel and controlled at a desired temperature from a flat die connected to an extruding machine and having a slit outflow portion, the plastic material being pressed and formed by the forming rolls therebetween and being carried out on a downstream side of the gap, the invention being characterized in that a temperature of the sheet is measured by directing non-contact temperature measuring means against the inner part of a wedge-shaped space formed by a surface of the sheet carried out of the gap and a surface of the forming roll opposite to the sheet surface at slight intervals.

The present invention further provides a measuring apparatus for measuring the temperature of a sheet carried out of a sheet forming apparatus wherein a plastic material, controlled at a desired temperature, is fed on an upstream side of a gap between a pair of rotating forming rolls arrayed almost in parallel and controlled at a desired temperature each relatively rotating with respect to each other from a flat die connected to an extruding machine and having a slit outflow portion, the plastic material being pressed and formed by the forming rolls therebetween and being carried out on a downstream side of the gap, the apparatus further comprising non-contact temperature measuring means and means for supporting the non-contact temperature measuring means so as to face on the inner part of a wedge-shaped space formed by a surface of the sheet carried out of the gap and a surface of the forming roll opposite to the sheet surface, at a slight intervals and also for scanning measured portions along the gap.

The aforementioned non-contact temperature measuring means will preferably be an infrared-ray radiating thermometer, and it is effective to construct the infrared-ray radiating thermometer to measure infrared-rays of an absorbing wave band of the sheet.

According to the characters of the present invention described above, a plastic material controlled at a desired temperature and fed on an upstream side of a gap of forming rolls, from a flat die connected to an extruding machine, is drawn into the gap by rotating of the forming rolls and cooled down by the forming rolls, controlled at a desired temperature suitable for forming and lower than the temperature of the plastic material, pressed and so formed therebetween, and carried out of a downstream side of the gap as a sheet. In this case, the cooling of the plastic material on the forming rolls is related to the quantity of, the bank. That is, the plastic material forming a bank is drawn into the gap to a sheet by the surfaces of the forming rolls on rotation of the rolls, therefore the plastic material having reached the gap is further cooled down during a long time of contact with the forming rolls in the instance where there is a large quantity of the bank, but to the contrary is cooled down but a little where the quantity of bank is small. Thus, the temperature of the sheet carried out of the gap is high if the quantity of bank is small, but the temperature becomes low if the quantity of bank is large. The invention therefore comprises monitoring the quantity of bank according to such knowledge.

With the relation between a temperature of the sheet carried out of the gap and the quantity of the bank, or the relation between the aforementioned temperature without relating directly to the quantity of the bank and a quality of a produced sheet grasped beforehand, the sheet forming method according to the invention comprises measuring a temperature of the sheet carried out of the gap, and controlling a portion relating to the quantity of bank which will be described next so as to adjust, for example, the temperature to a desired temperature according to a measured temperature information. That is, since the quantity of the bank changes according to a supply of the plastic material from the flat die, the rotational speed of the forming rolls and the size of the gap of the forming rolls, any one or a plurality of the forming conditions can be controlled.

A sheet temperature can be measured from a downstream side of the gap, and since there is no obstacle present on the downstream side, it can be measured with ease, and more accurate measurement will be secured by means, for example, of an infrared-ray radiating thermometer without contact thereof.

The sheet temperature is measured at plural positions in the cross direction or in full width continuously by scanning measuring positions in the cross direction thereof, a mean value is obtained thereby to the aforementioned control, and it is preferable in this case that a temperature distribution in the cross direction be further obtained to adjust a mechanism for adjusting a distribution of flow in the cross direction which is provided near the outflow portion of the flat die or a distribution in the cross direction of the gap of the forming rolls, thereby controlling a distribution in the cross-direction of the quantity of bank.

From measuring the inner part of a wedge-shaped space formed by a surface of the sheet carried out of the gap and a surface of the forming roll opposite to the sheet surface at slight intervals, a sheet temperature can be measured more accurately by the infrared-ray radiating thermometer on a cavity radiant effect as the forming roll surface is reflexible. Then, in the case of measurement on the infrared-ray radiating thermometer, a disturbance can be suppressed by measuring infrared-rays of an absorbing wave band of the sheet.

BRIEF DESCRIPTION OF THE DRAWINGS

In the accompanying drawings:

FIG. 10 is a flow-chart representing one example of a forming process;

DESCRIPTION OF THE PREFERRED EMBODIMENTS

Figure 1:
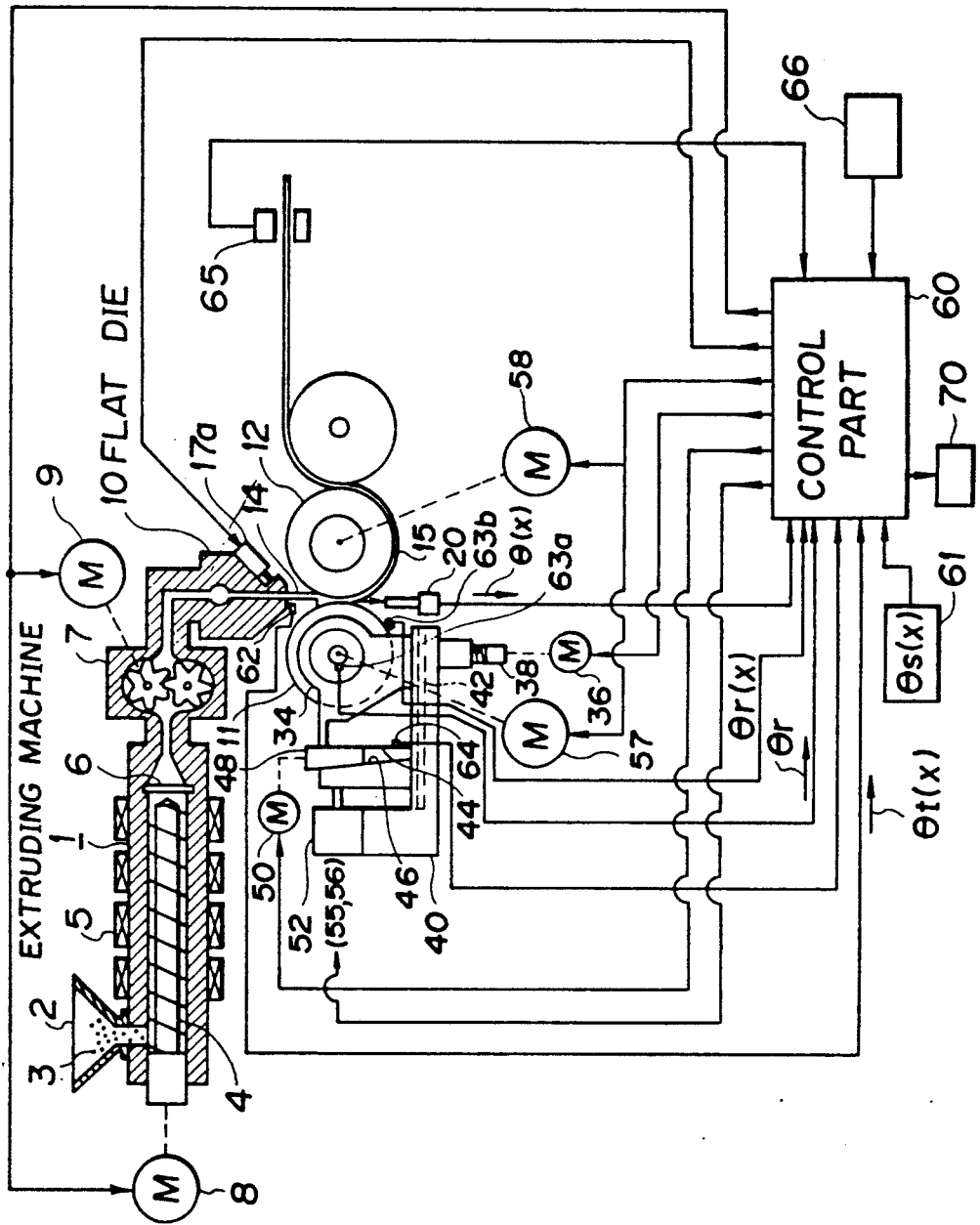
FIG. 1 is a block diagram of an operative example according to the present invention.

Preferred embodiments according to the present invention will now be described with reference to FIG. 1 to FIG. 10. In FIG. 1, reference numeral 1 denotes an extruding machine, delivery of a raw material 3 fed into a hopper 2, directly or by a measuring feeder, not shown on a screw 4, the raw material 3 being fused by heating on a shearing action according to the delivery and temperature control of a heating/cooling heat exchanger 5, and being then delivered to a flat die 10 by a gear pump 7 through a screen 6. Reference numeral 8 denotes a rotation driving motor for the screw 4, and 9 denotes a rotation driving motor for the gear pump 7.

Figure 2:
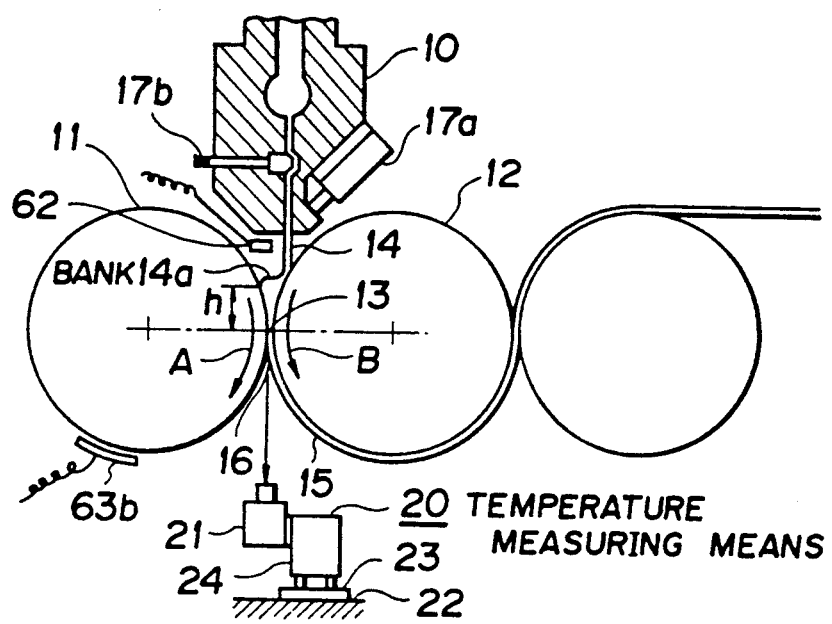
FIG. 2 is a fragmentary enlarged view of a sheet forming part and a sheet temperature measuring part.
Figure 7:
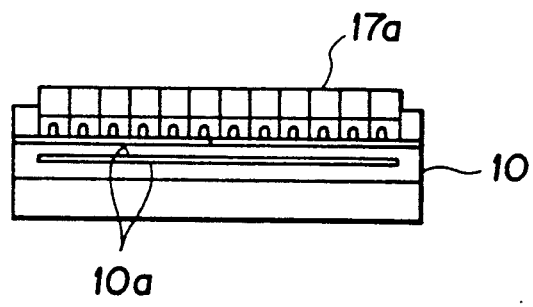
FIG. 7 is a drawing of flat die viewed from below in FIG. 1 and FIG. 2.

A heater (not shown) is mounted on the flat die 10, the plastic material 14, such as fused plastics, rubber or the like, which is delivered from the gear pump 7 is controlled at a desired temperature and fed to an upstream side of the gap 13 between the forming rolls 11, 12 as shown in FIG. 2. The heater mounted on the flat die 10 is constructed so as to determine a cross temperature distribution properly as known well hitherto. Then, mechanisms for adjusting a distribution of flow in the cross direction such as well-known lip adjusting device 17a, choke bar 17b, the heater and others are provided near a lip 10a which is an outflow portion of the flat die 10 as shown in FIG. 2 and FIG. 7, and thus a cross (horizontal in FIG. 7) distribution of the plastic material 14 discharged from the lip 10a can be adjusted.

Figure 8:
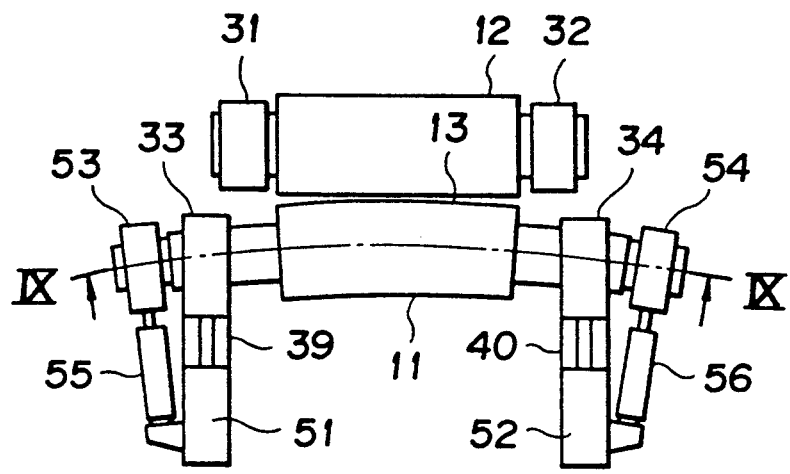
FIG. 8 is a schematic plan view of a bending control part for forming rolls.
Figure 9:
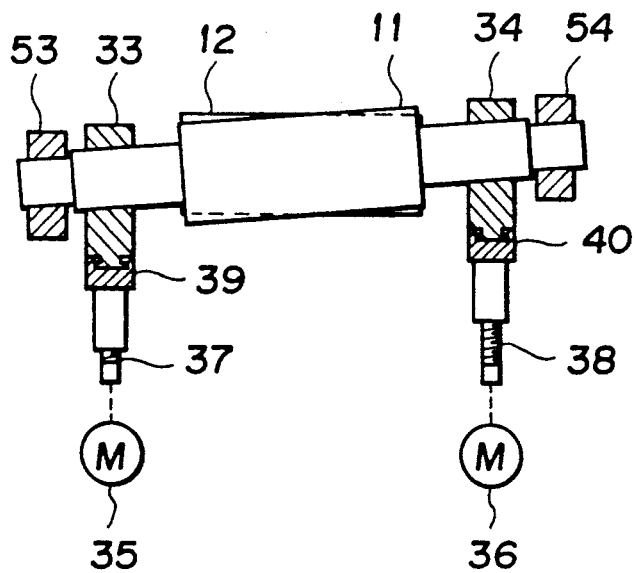
FIG. 9 is a sectional view taken on line IX—IX of FIG. 8.

The forming roll 12 is supported rotatably by bearings 31, 32 on its opposite ends as shown in FIG. 8, and the bearings 31, 32 are fixed on a frame which is not indicated therein. The forming roll 11 is supported rotatably by main bearings 33, 34 on the opposite ends thereof. Through both the forming rolls 11, 12 flows a thermally regulated fluid to the interior, which is controlled at a desired temperature. As shown in FIG. 1 and FIG. 9, the main bearings 33, 34 are mounted on moving beds 39, 40 movable vertically against the frame (not shown) by elevating devices 37, 38, such as screw or the like, which are driven by motors 35, 36 rotated relative to each other in the counter direction, and thus are ready for so-called roll cross control. As shown in FIG. 1, in which only the main bearing 34 side is shown, the main bearings 33, 34 are mounted movably by guides 41, 42 of the moving beds 39, 40 in the direction coming near to the forming roll 12. Stoppers 43, 44 are mounted on the moving beds 39, 40, taper blocks 45, 46 facing on the stoppers 43, 44 are provided on the main bearings 33, 34, and wedge-shaped gap adjusting members 47, 48 and a similar adjusting member on the other side of the roll (not shown) are interposed therebetween. Each of gap adjusting member 48 is moved vertically by a motor 50 and, hence, when the main bearings 33, 34 are pushed on a side of the forming roll 12 by pressure devices 51, 52, such as cylinder or the like, a size of the gap 13 between the forming rolls 11, 12 is set at a desired value.

As shown in FIG. 8, auxiliary bearings 53, 54 are mounted rotatably on end portions of the forming roll 11 coming further outward of the main bearings 33, 34. These auxiliary bearings 53, 54 are pulled downward (as viewed in FIG. 8) by driving devices 55, 56, such as cylinder or the like, which are mounted on the moving beds 39, 40, generating a force to bend the forming roll 11 in the direction indicated in FIG. 8 against a bank rolling force, and thus adjust a cross distribution of the gap 13 between the forming rolls 11, 12, which is ready for so-called roll bending control. The forming rolls 11, 12 are then rotated by motors 57, 58 shown in FIG. 1.

In FIG. 1 and FIG. 2, temperature measuring means 20 is provided on a downstream side of the gap 13 between the forming rolls 11, 12. The temperature measuring means 20 is for measuring a temperature of the sheet 15 carried out of the gap 13, and a non-contact infrared-ray radiating thermometer 21 is used in the example. The infrared-ray radiating thermometer 21 is directed against the inner part of a wedge-shaped space 16 (FIG. 2) formed by a surface of the sheet 15 carried out of the gap 13 and a surface of the forming roll 11 opposite thereto, and is constructed to measure a temperature of the sheet 15 on infrared-rays radiated from the surface of the sheet 15 immediately after coming out of the gap 13, or a surface temperature of the sheet 15 in the strict sense of the word. In case the infrared-ray radiating thermometer 21 is employed as temperature measuring means 20 like the example, while depending on an absorbing wave band of the sheet 15 or on the kind of the plastic material 14, it is preferable that the infrared ray be about 3.4 $\mu$m or so in wave length, measured generally in plastics, so as to suppress a disturbance caused by infrared rays radiated from those other than the sheet 15.

As shown in FIG. 2, the infrared-ray radiating thermometer 21 is mounted on a scanning head 24 shifting along a guide rail 23 provided on a frame 22. The guide rail 23 extends in parallel with the forming roll 12 and moves the infrared-ray radiating thermometer 21 along the gap 13 as the scanning head 24 shifts. The temperature measuring means 20 consisting of the infrared-ray radiating thermometer 21, the scanning head 24 and others generates a sheet temperature $\theta(\chi)$ intermittently in series or at proper intervals as temperature information, relating to a position of the scanning head 24, or a measuring position $\chi$ in the cross direction of the sheet 15. The output of the sheet temperature $\theta(\chi)$ is given to a control part 60 as shown in FIG. 1.

A desired value or set value $\theta\, s(\chi)$ is given to the control part 60 from a set temperature storage part 61, as shown in FIG. 1, corresponding to the sheet temperature $\theta\, (\chi)$. Then, outputs of a temperature sensor 62, such as infrared-ray radiating thermometer or the like, for detecting continuously a discharge temperature $\theta\, t(\chi)$ of the plastic material 14 discharged from the flat die 10 covering plural portions in the cross direction or full width thereof, a temperature sensor 63a for detecting a temperature $\theta\, r$ of the forming roll 11 from, for example, exit temperature of a fluid which controls the temperature and others, or a temperature sensor 63b for detecting a surface temperature $\theta\, r(\chi)$ of the forming roll 11 at plural portions or continuously in the cross direction are loaded in the control part 60.

Figure 4:
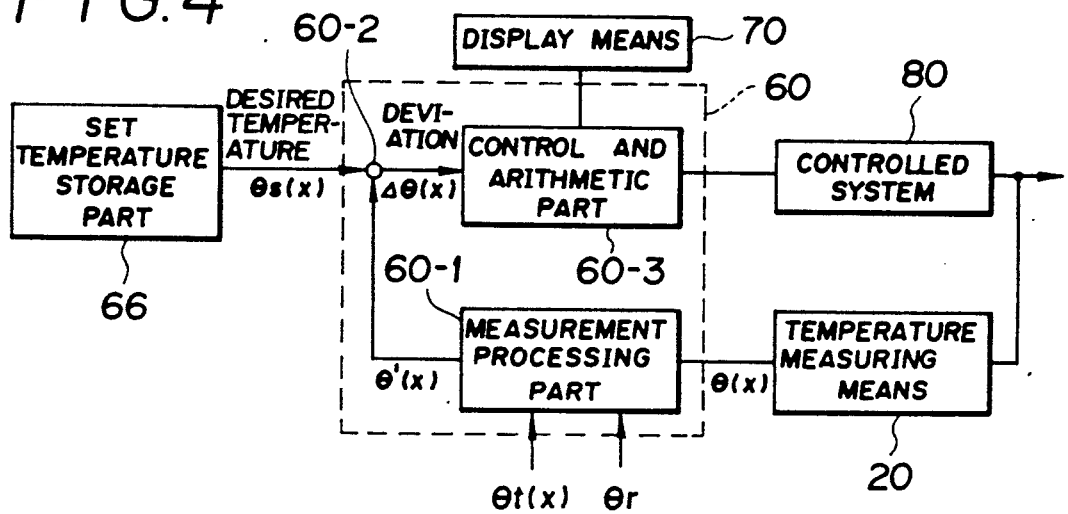
FIG. 4 is a block diagram showing a processing system for temperature detection.
Figure 6:
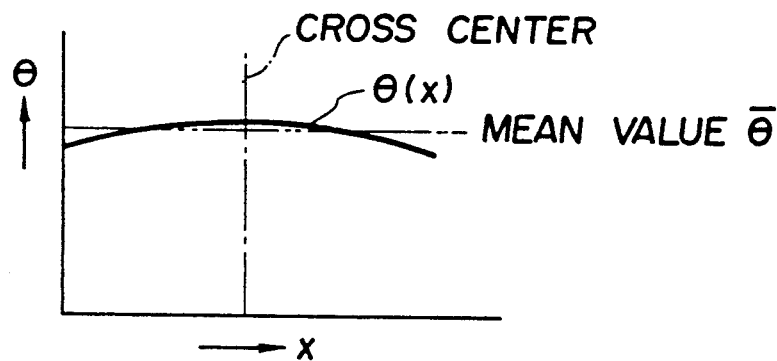
FIG. 6 is a drawing showing one example of a sheet temperature $\theta(\chi)$ corresponding to a measuring position $\chi$ in the cross direction of sheet.

As shown in FIG. 4, the control part 60 compares the sheet temperature $\theta\,(\chi)$ from the temperature measuring means 20 with the set value $\theta\, s(\chi)$ of the set temperature storage part 61 on a comparison part 60-2, obtains a deviation $\Delta\,\theta\,(\chi)$ corresponding to the measuring position $\chi$, and computes a deviation $\Delta\,\overline{\theta}$ of a mean value of the two in the cross direction of the sheet on a control and arithmetic part 60-3. In this case, the sheet temperature $\theta\,(\chi)$ changes according to the discharge temperature $\theta\, t(\chi)$ and roll temperature $\theta\, r(\chi)$ (or $\theta\, r$; hereinafter called simply $\theta\, r(\chi)$) and, therefore, in order to avoid an influence due to a change in these temperatures $\theta\, t(\chi)$, $\theta\, r(\chi)$, it is preferable that a correction is made to the sheet temperature $\theta\,(\chi)$ (or the set value $\theta\, s(\chi)$ otherwise) by a count processing part 60-1 shown in FIG. 4 according to these temperatures $\theta\, t(\chi)$, $\theta\, r(\chi)$. The aforementioned deviations $\Delta\,\overline{\theta}$ and $\Delta\,\theta\,(\chi)$ are displayed on display means 70. The display means 70 may display the sheet temperature $\theta(\chi)$ or $\theta'\,(\chi)$ obtained through the aforementioned correction, or may display a value obtained through conversion into the quantity of bank h on the control and arithmetic part 60-3.

When the sheet temperature $\theta\,(\chi)$ differs from the set value $\theta\, s(\chi)$ in the deviation $\Delta\,\overline{\theta}$ of mean values, the control and arithmetic part 60-3 of the control part 60 controls at least one set of various forming conditions such as rotational speeds of the motors 8, 9 for the screw 4 and the gear pump 7, rotational speeds of the driving motors 57, 58 for the forming rolls 11, 12, and rotational speeds of the shifting motors 49, 50 for the gap adjusting members 47, 48. Further, when there is the deviation $\Delta\,\theta\,(\chi)$ corresponding to the measuring position $\chi$, the control and arithmetic part 60-3 controls at least one of cross flow distribution adjusting mechanisms such as lip adjusting device 17a, choke bar 17b and others, the roll cross controlling motors 35, 36, and the driving devices 55, 56 for controlling the roll bending.

Figure 3:
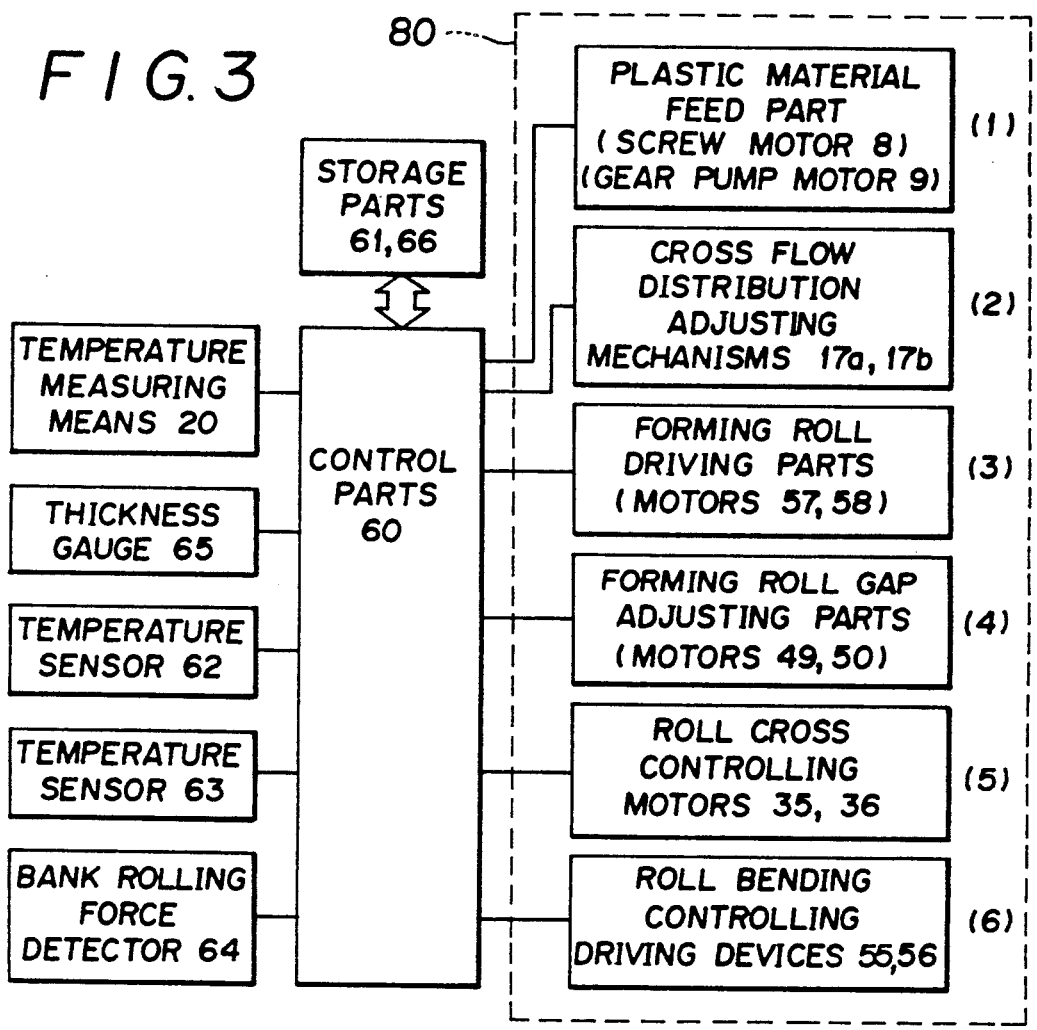
FIG. 3 is a main control block diagram.

FIG. 3 is a main control block diagram, in which the temperature measuring means 20, the temperature sensors 62, 63, a detector 64 for detecting a bank rolling force and a thickness gauge 65 which will be described hereinafter are connected to the control part 60, and measured values of temperature and thickness of the sheet 15, carried out of the forming rolls 11, 12 are inputted thereto as electrical signals. These signals are subjected to an arithmetic processing by CPU and others in the control part 60, and control signals are outputted to controlled systems 80 coming in the cross flow distribution adjusting mechanisms such as the screw motor 8 for the extruding machine 1 working as a plastic material feed part, the gear pump motor 9, the lip adjusting device 17a and others, the forming roll driving motors 57, 58, the motors 49, 50 for adjusting a gap between the forming rolls, the roll cross controlling motors 35, 36 and the driving devices 55, 56 for controlling the roll bending.

A control of the motors 49, 50 for adjusting a gap between the forming rolls, the roll cross controlling motors 35, 36, and the driving devices 55, 56 for controlling the roll bending relates to a bend of the forming rolls 11, 12 due to a bank rolling force generated in relation to the quantity of bank h, namely a force of the forming rolls 11, 12 for pressing the plastic material 14 therebetween and exerts an influence directly on a thickness of the produced sheet 15. Therefore, it is preferable that whether or not to control is set with reference to outputs from the detector 64 for detecting the bank rolling force and the thickness gauge 65. In FIG. 1, reference numeral 66 represents a storage part for the thickness set on the sheet 15.

The detector 64 for detecting the bank rolling force including a detection of a force working on the stopper 44 from the pressure device 52 through the taper block 46 and the gap adjusting member 48. In the embodiment, a system for obtaining the bank rolling force by deducting the force working on the stopper 44 which is detected on the detector 64 from an output or pressure of the pressure device 52 is exemplified, though it is not necessarily limitative.

A function of the apparatus will be described hereunder. The plastic material 14 fused on heat by the extruding machine 1 and controlled at a desired temperature by a heater provided on the flat die 10 which is not illustrated is discharged in sheet from the flat die 10 in the quantity according to rotational speeds of the screw 4 and the gear pump 7. The flat die 10 discharges the plastic material 14 on the cross flow distribution adjusting mechanisms such as the lip adjusting device 17a and others so as to have an almost equal supply distribution covering the full width.

As indicated in FIG. 2, the plastic material 14 discharged from the flat die 10 forms the bank 14a on an upstream side of the gap 13 between the forming rolls 11, 12, and is thrust half forcedly into the gap 13 on a luffing force of the forming rolls 11, 12 arising according to the quantity of bank h, pressed therebetween to the sheet 15, and is carried out on a downstream side of the gap 13.

In this case, the forming rolls 11, 12 are controlled normally at temperature $\theta\, r$ suitable for sheet forming which is lower than the discharge temperature $\theta\, t$ of the plastic material 14 discharged from the flat die 10 from having a fluid controlled at a predetermined temperature passed therebetween, therefore the plastic material 14 forming the bank 14a is cooled down by the forming rolls 11, 12 to the sheet 15.

Figure 5:
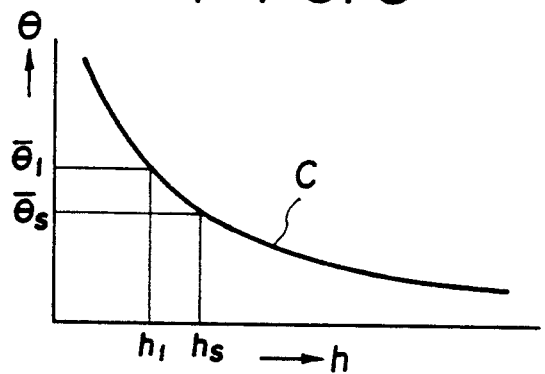
FIG. 5 is a drawing showing a relation between a temperature $\theta$ of sheet carried out and a quantity of bank h.

In this case, since a contact length of the plastic material 14 with the forming roll 11 is almost equal to the quantity of bank h, a surface temperature $\theta$ of the sheet 15 on a side of the forming roll 11 which is carried out of the gap 13 after passing through a portion of the bank 14a relatively at high speed takes a value relating to the quantity of bank h. FIG. 5 shows a relation between the surface temperature $\theta$ and the quantity of bank h. Then, the quantity of bank h is obtainable through the following equation:

$$h = f(\theta,\, \theta\, t,\, \theta\, r,\, t,\, T,\, A,\, B)$$

where $\theta$, $\theta t$, $\theta r$ denote a sheet temperature, a discharge temperature, a roll temperature respectively, t denotes a thickness of the sheet 15, T denotes a contact time of the plastic material 14 with the forming rolls 11, 12 which is determined according to a rotational frequency thereof, the letter A denotes a constant determined according to properties of the plastic material 14 such as specific heat, specific gravity, thermal conductivity and others, and letter B denotes a constant determined according to properties of the forming rolls 11, 12.

The sheet 15 carried out of the gap 13 parts from the forming roll 11 and is delivered on a side of the forming roll 12. The surface temperature $\theta$ of the sheet 15 carried out of the gap 13 on a side opposite to the forming roll 11 is measured by the temperature measuring means 20.

The infrared-ray radiating thermometer 21 of the temperature measuring means 20 is directed against the inner part of the wedge-shaped space 16 formed by a surface of the forming roll 11 and a surface of the sheet 15 opposite thereto. However, since both the surfaces are almost opposite to each other and the surface of the forming roll 11 is reflective against infrared rays, the aforementioned portion indicates a state akin to a so-called cavity radiation. Thus, the surface temperature $\theta$ of the sheet 15 is measured more accurately by the infared-ray radiating thermometer 21.

From having the measuring head 24 shifted repeatedly by the guide rail 23, the infrared-ray radiating thermometer 21 is scanned in the cross direction of the sheet 15, generating a sheet temperature $\theta$ ($\chi$) (FIG. 6) relating to the cross measuring position $\chi$, which is provided to the control part 60.

As shown in FIG. 4, the control part 60 compares the sheet temperature $\theta$ ($\chi$) with the set value $\theta$ s($\chi$) of the set temperature storage part 66 at the comparison part 60-2 while correcting it at the measurement processing part 60-1 according to a deviation of the temperature $\theta$ t($\chi$) of the plastic material 14 discharged from the flat die 10 which is provided from the temperature sensors 62, 63 shown in FIG. 1 and the temperature $\theta$ r-($\chi$) of the forming roll 11 to the set values thereof, outputs the deviation $\Delta \theta$ ($\chi$) corresponding to the measuring position $\chi$ of the two and computes the deviation $\Delta \overline{\theta}$ of a mean value of the two. Then, a correction of change in the sheet thickness t and the contact time T which are variables in the equation of the quantity of bank h is omitted in this embodiment.

In case, for example, a mean value $\overline{\theta}_1$ of the sheet temperature $\theta$ is higher than a mean value $\overline{\theta s(\chi)}$ of the set value $\theta$ s($\chi$), a quantity of bank $h_1$ at the time of measurement indicates a value lower than a desired value $h_s$, as will be apparent from FIG. 5. Now, therefore, the quantity of bank h is increased in full width, in this case, by reducing an interval of the gap 13 between the forming rolls 11, 12 according to an absolute value of the deviation $\Delta \overline{\theta}$. Accordingly, a similar effect is obtainable from increasing rotational speeds of the screw 4 and the gear pump 7 to increase a supply of the plastic material 14, or decreasing rotational speeds of the forming rolls 11, 12.

In a case, where there is the deviation $\Delta \theta$ ($\chi$) corresponding to the measuring position $\chi$; the quantity of bank h will be changed in part by adjusting the cross flow distribution adjusting mechanisms such as the lip adjusting device 17a shown in FIG. 7 and others, thereby adjusting a cross distribution of the quantity of bank h($\chi$) to a predetermined distribution.

The above-described embodiment has referred to a method for controlling the quantity of bank h($\chi$) at a desired value by measuring the temperature $\theta$ ($\chi$) of the sheet 15 carried out of the gap 13. While the quantity of bank h($\chi$) is the most important parameter for obtaining the quality sheet 15, it goes without saying that a similar effect is obtainable from quantifying beforehand the temperature $\theta$ ($\chi$) of the sheet 15 at which the quality sheet 15 is obtained, and taking the temperature itself as an object to control instead of the quantity of bank h($\chi$) directly therefor.

Here, as factors which exert an influence on a final thickness of the sheet 15, the quantity of bank h($\chi$), the cross thickness of the plastic material 14 fed from the flat die 10 and curves of the forming rolls 11, 12 are interrelated with each other as described hereinbefore.

Accordingly, for constructing an automation system for forming a sheet more uniform in thickness and warpless, it is necessary to carry out orderly (1) an adjustment of the cross flow distribution by the flat die 10, (2) an adjustment of the cross thickness distribution of the sheet 15 (roll cross, roll bending), and (3) an adjustment of the quantity of bank h.

FIG. 10 represents one example of a flowchart of a further concrete forming process using the apparatus described.

First, the sheet thickness as a forming target is set (Step 100).

Corresponding to a set point of the thickness, rotational speeds of the screw motor 8 of the extruding machine 1 and the gear pump motor 9, and the gap 13 between the forming rolls 11, 12 are initialized at predetermined values (Step 101).

Next, the extruding machine 1 is actuated to feed the plastic material 14 to the gap 13 between the forming rolls 11, 12, which is pressed and formed into sheet by the forming rolls 11, 12 in the gap 13 therebetween and carried out on a downstream side of the gap 13 for the initial forming, and then the thickness t of the sheet formed initially is measured (Step 102).

Then, rotational speeds of the forming rolls 11, 12 are controlled according to the thickness t of the measured sheet 15, thus deciding the basic sheet thickness t (mean value) (Step 103).

After these steps, the temperature $\theta$ ($\chi$) of the sheet 15 carried out of the gap 13 between the forming rolls 11, 12 is measured by the temperature measuring means 20. Then, as described above with reference to FIG. 4, a fine control is made so as to adjust the measured temperature information $\theta$ ($\chi$) to the value $\theta$ s($\chi$) given beforehand corresponding to the desired quantity of bank hs($\chi$) by the cross flow distribution adjusting mechanisms, such as lip adjusting device 17a of the flat die 10, and others (Step 104, Step 105).

Further, a thickness t($\chi$) of the sheet 15 is measured and a control is carried out for the roll bending and the roll cross as occasion demands (Step 106, Step 107).

An initial set sheet thickness is obtained finally through these steps.

Figure 11A:
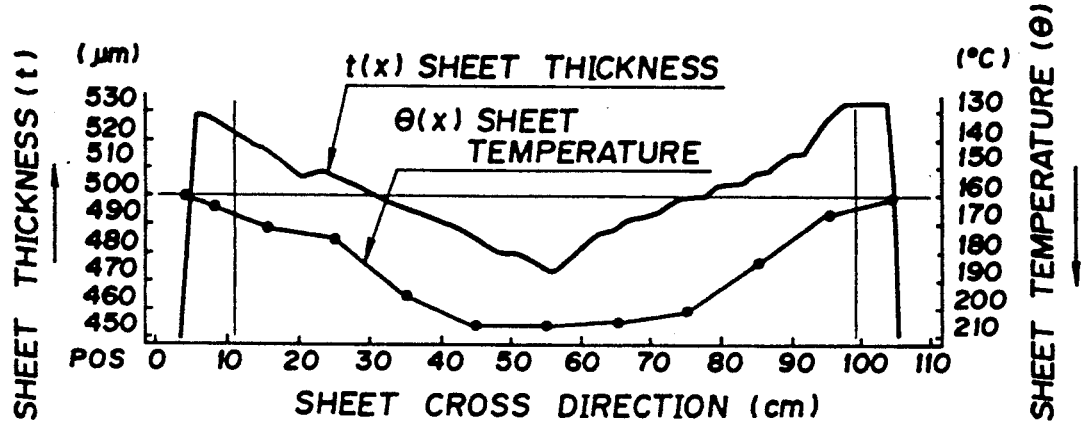
FIGS. 11A to 11C are views showing a relation between sheet temperature $\theta(\chi)$ and sheet thickness $t(\chi)$ in a process for flattening the sheet temperature $\theta(\chi)$.
Figure 11B:
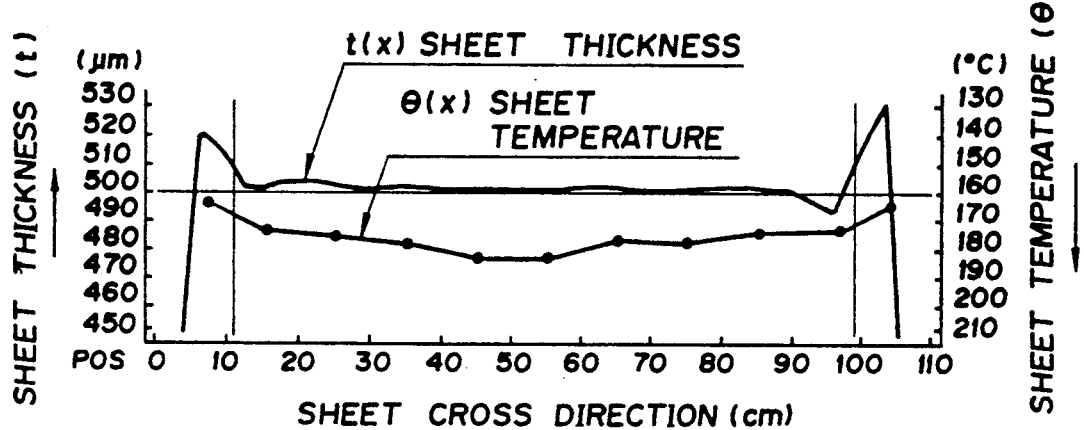
Figure 11C:
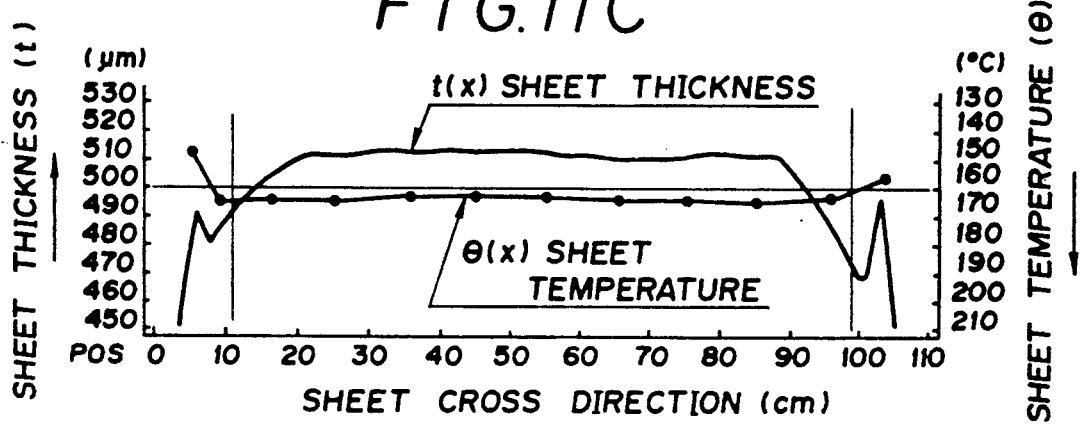

FIGS. 11A to 11C represent synchronization measuring position taken from measuring the sheet temperature $\theta$ ($\chi$) and the sheet thickness t($\chi$) at time difference when a sheet forming test was carried out by means of the temperature measuring means 20 and the sheet thickness gauge 65. For easy understanding of a correlation between the sheet temperature $\theta$ and the sheet thickness t, the directions in which a graduation increases are inverted in FIGS. 11A to 11C. The plastic material used for the test was polycarbonate (PC), a width and discharge of the flat die 10 were 1,100 mm and 160 kg/H respectively, and a discharge temperature $\theta$ t from the flat die 10 and a temperature $\theta$ r of the forming rolls 11, 12 were set and so controlled at 275° C. and 140° C. respectively.

Essentially, it is desirable that a correlation between the quantity of bank $h(\chi)$ and the temperature $\theta$ ($\chi$) of the sheet 15 measured on the temperature measuring means 20 is ensured directly through a test. However, since it is very difficult to measure the quantity of bank $h(\chi)$ directly for the reason mentioned hereinabove, a distance between the flat die 10 and the forming rolls 11, 12 was kept appreciably longer than that at the time of practical sheet forming, thereby ensuring the quantity of bank $h(\chi)$ with the naked eye. Further, a pressure of the forming rolls 11, 12 was controlled to be lower than that at the time of practical sheet forming so as to minimize a flexure of the forming rolls 11, 12, and thus the test was carried out with a size of the gap 13 between the forming rolls 11, 12 kept as constant as possible.

Thus, the thickness t of the sheet 15 was allowed to have a high positive correlation with the quantity of bank h, being thick almost proportionally when the quantity of bank h was large but thin when small.

FIG. 11A represents an initial state of the sheet forming under special forming conditions as described above. As will be apparent therefrom, the sheet thickness $t(\chi)$ and the sheet temperature $\theta$ ($\chi$) have a good negative correlation with each other. Accordingly, for the reasons mentioned above, the sheet temperature $\theta$ ($\chi$) can also be regarded as having a good correlation with the quantity of bank $h(\chi)$. Practically, the quantity of bank h on opposite end portions of the sheet was noticeably large and the quantity of bank h at the center was small by visual observation, and thus a good correlation could be found between the sheet temperature $\theta$ ($\chi$) and the quantity of bank $h(\chi)$. Then, in the formed state, since the quantity of bank h at the sheet center was insufficient, a surface loss called "shrink mark" arose and further since the quantity of bank was excessive at opposite end portions of the sheet, there arose a surface loss called "bank mark". Thus, the surface losses can be foreknown by estimating the quantity of bank $h(\chi)$ from the sheet temperature $\theta$ ($\chi$), therefore the sheet temperature $\theta$ ($\chi$) is very effective for detection of the sheet surface loss.

FIG. 11B represent a state wherein an interval between the flat die 10 and the forming rolls 11, 12 is contracted as compared with the state of FIG. 11A, the gap 13 is minimized to increase the roll pressure, thereby setting practical sheet forming conditions. A distribution of the gap 13 of the flat die 10 is adjusted and a distribution of the cross thickness at the sheet center is corrected flat. As a result, as will be apparent therefrom, the sheet thickness t is almost flat except, at opposite end portions of the sheet, but the sheet temperature $\theta$ ($\chi$) is somewhat high in distribution at the sheet center. The reason is that the quantity of bank h is small at the sheet center as compared with opposite end portions, and the quantity of bank h is large at opposite end portions of the sheet as compared with the center.

A phenomenon wherein the quantity of bank $h(\chi)$ is small at the sheet center but large at opposite end portions thereof as described above is so cause, because the sheet thickness distribution $t(\chi)$ is flat, but the forming rolls 11, 12 are bent due to the force of pressing the sheet, and the gap 13 is so big and is larger at the roll center than at opposite end portions thereof. Under such forming conditions, since the sheet thickness is flat to some extent but the quantity of bank h is uneven, a sheet surface loss is easy to arise, and thus a homogeneous sheet is hard to obtain, which is not preferable. That is, while the sheet thickness $t(\chi)$ is flat, the sheet surface loss may arise from improper quantity of bank h, and a continuous supervision of the quantity of bank h will be indispensable.

FIG. 11C represents a state wherein a cross flow distribution of the flat die 10 is adjusted and rotational speeds of the forming rolls 11, 12 are also adjusted to flatten the sheet temperature $\theta$ ($\chi$) to a certain value for flattening the quantity of bank $h(\chi)$ against FIG. 11B. As will be apparent therefrom, while the sheet temperature $\theta$ ($\chi$) is flat, the sheet thickness $t(\chi)$ has a convex distribution thicker at the sheet center but thinner at opposite end portions thereof excluding edge portions. The reason is that since the quantity of bank h is uniform, the aforementioned roll flexure has caused the convex distribution.

As described, a quality sheet uniform and free from a surface loss with the quantity of bank h given at a desired value can be formed by flattening the sheet temperature $\theta$ ($\chi$) to a desired value. However, the sheet thickness distribution becomes convex due to the roll flexure. In a formed state of FIG. 11C, an ideal and quality sheet flat in thickness convering the full width can be formed even in a uniform bank state from using a crowning roll or a roll flexure correcting mechanism such as roll bending, roll cross or the like. The above-described embodiment exemplifies a case where the temperature $\theta$ ($\chi$) of the sheet 15 coming out of the gap 13 is measured and the forming conditions are adjusted automatically according to the result obtained therefrom, but it is most important to grasp beforehand the quantity of bank $h(\chi)$ securely, and, needless to say, the forming conditions may be adjusted by hand accordingly.

Further, since the sheet temperature $\theta$ is measured at a position very near to a sheet outlet from the flat die 10, a time lag in the control is exceedingly short as compared with a sheet thickness gauge or the like. Thus, a precise control is realizable even at the time when a fluctuation may easily arise during the initial sheet forming, and forming conditions for obtaining a desired sheet product at a very short time may be secured. Further, the system is ready to answer for various disturbances, and thus a quality sheet can be formed at an exceedingly high yield.

What is claimed is:

1. A method of monitoring quantity of bank in sheet forming which is carried out by a sheet forming apparatus which comprises means for feeding a plastic material controlled at a predetermined temperature, a pair of forming rolls arrayed substantially in parallel with each other with a predetermined gap therebetween for pressing and forming the plastic material into a sheet and a control unit for controlling the operation of the feeding means and the forming rolls, and in which a plastic material with a controlled predetermined temperature is formed into a sheet by forming a bank of the plastic material on an upstream side of the gap between the forming rolls and the plastic material then being fed to a downstream side of the gap, the method comprising the steps of:

storing in the control unit a preliminarily obtained relationship between information of a temperature of the plastic material just after it has been fed through the gap between the forming rolls and the quantity of the bank;

measuring a temperature of the plastic material having a sheet shape just after it has passed through the gap between the forming rolls;

inputting a measured temperature information of the plastic material sheet into the control unit;

calculating a quantity of bank corresponding to the measured temperature information; and displaying the calculated quantity of the bank.

2. The monitoring method as defined in claim 1, wherein temperature information of the sheet to be measured indicates a temperature distribution of at least a plurality of portions in a cross direction of the sheet fed through the gap between the forming rolls and a distribution of the bank quantity in a cross direction thereof.

3. The monitoring method as defined in claim 1, wherein the quantity of the bank is calculated by correcting temperature information of the measured sheet according to temperature information of the plastic material fed on an upstream side of the gap.

4. The monitoring method as defined in claim 1, wherein the quantity of the bank is calculated by correcting temperature information of the measured sheet according to temperature information of the forming rolls.

5. The monitoring method as defined in claim 1, wherein a temperature of said sheet is measured by directing a non-contact type temperature measuring means against an inner part of a wedge-shaped space formed by a surface of the sheet fed through the gap between the forming rolls and a surface of at least one forming roll opposite to the surface of the sheet.

6. An apparatus for monitoring quantity of bank in a sheet forming machine which comprises means for feeding a plastic material controlled at a predetermined temperature, a pair of forming rolls arrayed substantially in parallel with each other with a predetermined gap therebetween for pressing and forming the plastic material into a sheet and a control unit for controlling the operation of the feeding means and the forming rolls, and in which a plastic material with a controlled predetermined temperature is formed into a sheet by forming a bank of the plastic material on an upstream side of the gap between the forming rolls and the plastic material then being fed to a downstream side of the gap, the apparatus comprising:

means for measuring a temperature of the plastic material sheet passing through the gap between the forming rolls;

means for calculating the quantity of the bank in response to information of the measured temperature from the temperature measuring means and a relationship between the measured temperature information and the quantity of the bank which is preliminarily stored in the control unit; and means for displaying information of the quantity of the bank inputted from the calculating means.

7. The monitoring apparatus as defined in claim 6, wherein said temperature measuring means is constructed to measure temperatures of at least a plurality of portions in a cross direction of the sheet fed through the gap between the forming rolls and said display means is constructed to display a distribution of the quantity of the bank in a cross direction thereof.

8. The monitoring apparatus as defined in claim 6 further comprising a first temperature sensor for detecting temperature of the plastic material fed to the gap between the forming rolls and a first measurement processing element connected between said temperature measuring means and said calculating means for correcting the temperature information according to an output of said first temperature sensor.

9. The monitoring apparatus as defined in claim 8, further comprising a second temperature sensor for detecting a temperature of said forming rolls and a second measurement processing element connected between said temperature measuring means and said calculating means for correcting the temperature information according to an output of said second temperature sensor.

10. The monitoring apparatus as defined in claim 9, wherein said first and second temperature sensors detect temperatures of at least a plurality of portions in a cross direction, respectively.

11. The monitoring apparatus as defined in claim 6, wherein said temperature measuring means is an infrared-ray radiating thermometer and is mounted to face on an inner portion of a wedge-shaped space formed by a surface of the sheet fed through the gap between the forming rolls and a surface of at least one of the forming rolls opposite to the surface of the sheet.

12. The monitoring apparatus as defined in claim 11, wherein the infrared-ray radiating thermometer measures infrared-ray of an absorbing wave band of the sheet.

13. A method of forming a sheet carried out by utilizing a sheet forming machine which comprises means for feeding a plastic material controlled at a predetermined temperature, a pair of forming rolls arrayed substantially in parallel with each other with a predetermined gap therebetween for pressing and forming the plastic material into a sheet and a control unit for controlling the operation of the feeding means and the forming rolls, and in which the plastic material with a controlled predetermined temperature is formed into a sheet by forming a bank of the plastic material on an upstream side of the gap between the forming rolls and the plastic material is then fed to a downstream side of the gap, the method comprising the steps of:

measuring a temperature of the plastic material sheet fed through the gap between the forming rolls; and controlling various forming conditions according to a measured temperature information.

14. The forming method as defined in claim 13, wherein the forming condition being controlled is a supply of the plastic material to the gap between the forming rolls.

15. The forming method as defined in claim 13, wherein the forming condition being controlled is a rotational speed of the forming rolls.

16. The forming method as defined in claim 13, wherein the forming condition being controlled is a gap between the forming rolls.

17. The forming method as defined in claim 13, wherein temperature information of the plastic material sheet to be measured indicates a temperature distribution consisting of at least a plurality of positions in a cross direction of the plastic material sheet fed through the gap between the forming rolls.

18. The forming method as defined in claim 17, wherein a reference set temperature information to temperature information of the plastic material sheet to be measured is specified as indicating a distribution corresponding to the temperature distribution in a cross direction of the plastic material to be fed.

19. A method of forming a sheet by utilization of a sheet forming machine including an extruder, a flat die and a pair of forming rolls, comprising the steps of:

setting a working thickness as a forming target of a sheet to be formed;

initiating a supply of a plastic material from the extruding machine and setting a gap of a pair of the forming rolls for forming a sheet according to the set thickness;

feeding the plastic material to the gap between the forming rolls from the flat die connected to the extruding machine and having a slit outflow portion, pressing and forming the plastic material on the forming rolls therebetween while simultaneously forming a bank of the plastic material on an upstream side of the gap between the forming rolls and feeding the plastic material to a downstream side of the gap as a sheet;

initiating a rotational speed of the forming rolls according to a mean thickness of the initial sheet;

measuring a temperature of the sheet fed through the gap between the forming rolls; and adjusting a mechanism for adjusting a distribution of flow of plastic material running breadthwise which mechanism is provided at least near an outflow portion of the flat die so as to adjust the measured temperature of the sheet to a predetermined value correspondingly to a predetermined quantity of the bank, thereby adjusting the quantity of the bank.

20. The forming method as defined in claim 19, further comprising the steps of measuring a thickness of the sheet fed through the forming rolls after the quantity of the bank is adjusted and adjusting a distribution in the cross direction of the gap between the forming rolls according to the measured value.

21. A sheet forming apparatus of a sheet forming machine which comprises means for feeding a plastic material controlled at a predetermined temperature, a pair of forming rolls arrayed substantially in parallel with each other with a predetermined gap therebetween for pressing and forming the plastic material sheet and a control unit for controlling the operation of the feeding means and the forming rolls, and in which the plastic material with a controlled predetermined temperature is formed into a sheet by forming a bank of the plastic material on an upstream side of the gap between the forming rolls and the plastic material then being fed to a downstream side of the gap, the apparatus further comprising:

means for measuring a temperature of the plastic material sheet fed through the gap between the forming rolls; and means for controlling various forming conditions in accordance with information of the measured temperature of the plastic material sheet.

22. The sheet forming apparatus as defined in claim 21, wherein the means being controlled is a plastic material feed part of the feeding means.

23. The sheet forming apparatus as defined in claim 22, wherein the means being controlled is a rotation driving part of the forming rolls.

24. The sheet forming apparatus as defined in claim 22, wherein the means being controlled is a gap adjusting part of the forming rolls.

25. The sheet forming apparatus as defined in claim 22, wherein said temperature measuring means is constructed so as to generate outputs in relation to at least a plurality of measuring positions in a cross direction of the sheet.

26. The sheet forming apparatus a defined in claim 22, wherein said temperature measuring means is constructed so as to scan measured portions of the sheet in a cross direction of the sheet and also constructed so as to generate outputs in relation to each measured portion in a cross direction.

27. The sheet forming apparatus as defined in claim 22, wherein a reference set temperature information to temperature information of the sheet to be measured varies according to respective positions in a cross direction of the sheet.

28. The sheet forming apparatus as defined in claim 22, wherein the feeding means comprises an extruder for extruding the plastic material to a flat die having a slit outflow portion and a gear pump for delivering the plastic material toward the flat die from the extruder.

29. The sheet forming apparatus as defined in claim 28, wherein the means being controlled by said control means is a rotational screw of the extruder and the gear pump.

30. The sheet forming apparatus as defined in claim 28, wherein the means being controlled is a mechanism for adjusting a distribution of flow running in a cross direction of the flat die connected to the extruder.

31. The sheet forming apparatus as defined in claim 22, wherein said temperature measuring means is of a non-contact type measuring means.

32. The sheet forming apparatus as defined in claim 22, wherein said temperature measuring means is an infrared-ray radiating thermometer.

33. A method of measuring a temperature of a sheet carried out in a sheet forming machine which comprises means for feeding a plastic material controlled at a predetermined temperature, a pair of forming rolls arrayed substantially in parallel with each other with a predetermined gap therebetween for pressing and forming the plastic material into a sheet and a control unit for controlling the operation of the feeding means and the forming rolls, and in which a plastic material with a controlled predetermined temperature is formed into a sheet by forming a bank of the plastic material on an upstream side of the gap between the forming rolls and the plastic material then being fed to a downstream side of the gap, the method comprising the steps of:

providing a non-contact type temperature measuring means;

directing the non-contact type temperature measuring means against an inner portion of a wedge-shaped space formed by a surface of the sheet fed through the gap between the forming rolls and a surface of at least one of the forming rolls facing on the surface of the sheet with a gap therebetween; and measuring a temperature of the sheet fed through the gap between the forming rolls.

34. An apparatus for measuring a temperature of a sheet in a sheet forming machine which comprises means for feeding a plastic material controlled at a predetermined temperature, a pair of forming rolls arrayed substantially in parallel with each other with a predetermined gap therebetween for pressing and forming the plastic material sheet and a control unit for controlling the operation of the feeding means and the forming rolls, and in which a plastic material with a controlled predetermined temperature is formed into a sheet by forming a bank of the plastic material on an upstream side of the gap between the forming rolls and the plastic material then being fed to a downstream side of the gap, the apparatus comprising:

- a non-contact type temperature measuring means disposed on a downstream side of the forming rolls; and
- means for supporting the non-contact type temperature measuring means to face on an inner portion of a wedge-shaped space formed by a surface of the sheet fed through the gap between the forming rolls opposite to the surface of the sheet with a gap therebetween and for scanning the non-contact type temperature measuring means on portions to be measured along the gap.

35. The measuring apparatus as defined in claim 34, wherein the non-contact type temperature measuring means is an infrared-ray radiating thermometer.

36. The measuring apparatus as defined in claim 35, wherein said infrared-ray radiating thermometer measures infrared-ray of an absorbing wave band of the sheet.

37. An apparatus for measuring a temperature of a sheet in a sheet forming machine which comprises means for feeding a plastic material controlled at a predetermined temperature, a pair of forming rolls arrayed substantially in parallel with each other with a predetermined gap therebetween for pressing and forming the plastic material into a sheet and a control unit for controlling the operation of the feeding means and the forming rolls, and in which a plastic material with a controlled predetermined temperature is formed into a sheet by forming a bank of the plastic material on an upstream side of the gap between the forming rolls and the plastic material then being fed to a downstream side of the gap, the apparatus comprising:

- means for measuring temperatures of at least a plurality of portions of the sheet fed through the gap between the forming rolls along a cross direction of the sheet; and
- means for displaying a temperature distribution of the sheet along the cross direction thereof in accordance with information regarding the temperatures measured by the temperature measuring means.

38. The temperature measuring apparatus as defined in claim 37, wherein said temperature measuring means is constructed so as to scan the measured portion in the cross direction of the sheet and also constructed so as to generate outputs in relation to each measuring position in a cross direction.

* * * * *